United States Patent [19]
Habener et al.

[11] Patent Number: 5,919,649
[45] Date of Patent: Jul. 6, 1999

[54] CAMP-RESPONSIVE TRANSCRIPTIONAL ENHANCER BINDING PROTEIN

[75] Inventors: Joel F. Habener, Newton Highlands, Mass.; James P. Hoeffler, Evergreen, Colo.

[73] Assignee: The General Hospital Corporation, Boston, Mass.

[21] Appl. No.: 07/684,965

[22] PCT Filed: Nov. 20, 1989

[86] PCT No.: PCT/US89/05234

§ 371 Date: May 22, 1991

§ 102(e) Date: May 22, 1991

[87] PCT Pub. No.: WO07/68496

PCT Pub. Date: May 22, 1991

Related U.S. Application Data

[63] Continuation-in-part of application No. 07/272,980, Nov. 18, 1988, abandoned.

[51] Int. Cl.$^6$ .......................... C12P 21/00; C12N 15/85; C12N 5/10; C07H 21/04
[52] U.S. Cl. ..................... 435/69.1; 435/254.11; 435/320.1; 435/325; 435/455; 435/463; 536/23.1; 536/23.5; 536/24.1; 536/24.5
[58] Field of Search ................. 435/69.1, 172.3, 435/320.1, 254.11, 325, 455, 463; 530/358; 536/23.1, 23.5, 24.1, 24.5

[56] References Cited

PUBLICATIONS

Singh et al. (Feb. 1988), Cell 52: 415–423.
Montminy et al. (Jul. 1987), Nature 328: 175–178.
Dynan, W.S. et al., *Nature* 316:774–778 (1985).
Montminy, M.R. et al., *Proc. Natl. Acad. Sci. USA 83*: 6682–6686 (1986).
Silver, B.J. et al., *Proc. Natl. Acad. Sci. USA 84*: 2198–2202 (1987).
Jameson, J.L. et al., *Endocrinology 119* (6): 2560–2567 (1986).
Delegeane, A.M. et al., *Mol. Cell. Biol. 7(11)*:3994–4002 (1987).
Jameson, J.L. et al., *Mol. Cell. Biol. 7(9)*:3032–3040 (1987).
Deutsch, P.J. et al., *J. Biol. Chem. 262(25)*:12169–12174 (1987).
Short, J.M. et al., *J. Biol. Chem. 261(21)*:9721–9726 (1986).
Lewis, E.J. , *Proc. Natl. Acad. Sci. USA 84*:3550–3554 (1987).
Angel, P. et al., *Cell 49*:729–739 (1987).
Tsukada, T. et al., *J. Biol. Chem. 262(18)*:8743–8747 (1987).
Comb, M. et al., *Nature 323*:353–356 (1986).
Lee, W. et al., *Cell 49*:741–752 (1987).
Deutsche, P.J. et al., *Proc. Natl. Acad. Sci. USA 85*:7922–7926 (1988).
Knecht, D.A. et al., *Science 236*:1081–1086 (1987).
Cabrera, C.V. et al., *Cell 50*:659–663 (1987).
Landschulz, W.H. et al., *Science 240*1759–1764 (1988).
Sigler, P.S. *Nature 333*:210–212 (1988).
Bohmann, D. et al., *Science 238*:1386–1392 (1987).
Angel, P. et al., *Nature 332*:166–171 (1988).
Hardy, S. et al., *Proc. Natl. Acad. Sci. USA 85*:4171–4175 (1988).
Hoeffler et al., *Science 242*:1430–1433 (1988).
Marx, Jean L., *Science 242*:1377–1378 (1988).
Deutsch et al., *J. Biol. Chem. 263(34)*:18466–18472 (1988).
Genbank Accession No. M27691 (DNA sequence of CREB protein), release date was between Nov. 15 and Nov. 30, 1989.

*Primary Examiner*—David Guzo
*Attorney, Agent, or Firm*—Sterne, Kessler, Goldstein & Fox p.l.l.c.

[57] ABSTRACT

This invention is directed toward the characterization and cloning of a cAMP-responsive transcription enhancer binding protein (CREB). This protein, CREB, is a transcriptional activator which activates transcription in eukaryotic cells. This CREB protein can be used to increase or decrease production of proteins by stimulating expression of a recombinant gene that is operably-linked to the CRE enhancer element and responsive to cAMP.

20 Claims, 9 Drawing Sheets

FIG. 1A

Translation of CREBCDNA3 over region 126-1106;.

```
         10         20         30         40         50         60
GAA TTC GGG CGC GCC GGA CGC CCG GGT GTA GTT CAA GGT GTG TTA CGT GGG GGA GAG AAT AAA
CTT AAG CCC GCG CCG CCT CCA CAT CAA ACT GCG CCA AAT GCA CAC CCC CTC TTA TTT
                    70         80         90        100        110        120
ACT CCA GCG AGA TCC GCG CCG TGA ACG AAA GCA GTG ACG GAG CTT GTA CCA CCG GTA
TGA GGT CGC TCT AGG CGC GGC ACT TGC TTT CGT CAC TGC CTC GAA CAT GGT GGC CAT 130        140        150        160        170
ACT AA ATG ACC ATG GAA TCT GGA GCC GAG AAC CAG CAG GGA CAT CTA GCA GCT GTA ACA
TGA TT TAC TGG TAC CTT AGA CCT CGG CTC TTG GTC GTC CCT GTA GAT CGT CCA CAT TGT
         M   T   M   E   S   G   A   E   N   Q   Q   G   D   L   A   A   V   T—

180        190        200        210        220        230
GAA GCT GAA AAC CAA CAA GTT ACA CAA GCC CAG GTC CCA CAG GGA CAT CTA TTA GCC CAG
CTT CGA CTT TTG GTT GTT CAA TGT GTT CGG GTC CAG GGT GTC CCT GTA GAT CGG GTC
 E   A   E   N   Q   Q   V   T   Q   A   Q   V   P   Q   G   H   L   L   A   Q↓

240        250        260        270        280        290
GTA TCT ATG CCA GCA GCT CGA GCA ACA TCA TCT GCT CCC ACC GTA ACT CTA GTA CAG CTG
CAT AGA TAC GGT CGT CGA GCT CGT TGT AGT AGA CGA GGG TGG CAT TGA GAT CAT GTC GAC
 V   S   M   P   A   A   R   A   T   S   S   A   P   T   V   T   L   V   Q   L↓

300        310        320        330        340        350
CCC AAT GGG CAG ACA GTT CAT GTC CAT GGA GTC ATT CAG GCG GCG CCC AGG GTC CCA TCA
GGG TTA CCC GTC TGT CAA GTA CAG GTA CCT CAG TAA GTC CGC CGC GGG TCC CAG AGT
 P   N   G   Q   T   V   H   V   H   G   V   I   Q   A   A   P   S   V   Q↓

360        370        380        390        400        410
CAG GTC ACA CAA GTT CAG GTT CAA ACA GTT CAG GTT CAG ATT TCA ACT ATT GCA GAA CAT TCA CAG
GTC CAG TGT GTT CAA GTC CAA GTT TGT CAA GTC CAA GTC TAA AGT TGA TAA CGT CTT GTA AGT GTC
 Q   V   T   Q   V   Q   V   Q   T   V   Q   V   Q   I   S   T   I   A   E   S↓

420        430        440        450        460        470
GAG TCA GTG GAT AGT GTA ACT GAT TCC CAA AAC CGA GAA ATT CTT TCA AGG AGG CCT
CTC AGT CAC CTA TCA CAT TGA CTA AGG GTT TTG GCT CTT TAA GAA AGT TCC TCC GGA
 E   S   V   D   S   V   T   D   S   Q   N   R   E   I   L   S   R   R   P—
```

```
480                                       490                                       500                                       510                                       520                                       530
TCC TAC AGG AAA ATT TTG AAT GAC TTA TCT TCT GAT GCA CCA GGA GTG CCA AGG ATT GAA
AGG ATG TCC TTT TAA AAC TTA CTG AAT AGA AGA CTA CGT GGT CCT CAC GGT TCC TAA CTT
 S   Y   R   K   I   L   N   D   L   S   S   D   A   P   G   V   P   R   I   E 540                                       550                                       560                                       570                                       580                                       590
GAA GAG AAG TCT GAA GAG ACT AGC CTC GAG ACT TCA GCA CCT GCC ATC ACC ACT GTA ACG GTG CCA ACT
CTT CTC TTC AGA CTT CTC TGA TCG GAG CTC TGA AGT CGT GGA CGG TAG TGG TGA CAT TGC CAC CGT TGA
 E   E   K   S   E   E   T   S   L   E   T   S   A   P   A   I   T   T   V   T 600                                       610                                       620                                       630                                       640                                       650
CCA ATT TAC CAA ACT AGC AGT GGA CAG CAG TAT ATT GCC ATT ACC CAG GGA GCA ATA CAG
GGT TAA ATG GTT TGA TCG TCA CCT GTC GTC ATA TAA CGG TAA TGG GTC CCT CGT TAT GTC
 P   I   Y   Q   T   S   S   G   Q   Q   Y   I   A   I   T   Q   G   A   I   Q 660                                       670                                       680                                       690                                       700                                       710
CTG GCT AAC AAT GGT ACC TGG CTA CCC CAT GGG GTA CAG GGC CTG GAC CAA GTT TGT ACC AAT GCA
GAC CGA TTG TTA CCA TGG ACC GAT GGG GTA CCC CAT GTC CCG GAC CTG GTT CAA ACA TGG TTA CGT
 L   A   N   N   G   T   W   L   P   H   G   V   Q   G   L   D   Q   V   C   T   N   A 720                                       730                                       740                                       750                                       760                                       770
GCA GCC ACT CAG CCG GGT CCA ACC ATT CTA CAG TAT GCA GCT GCC TCT GGA GAC CTG GGA CAG CAG
CGT CGG TGA GTC GGC CCA GGT TGG TAA GAT GTC ATA CGT CGA CGG AGA CCT CTG GAC CCT GTC GTC
 A   A   T   Q   P   G   P   T   I   L   Q   Y   A   A   A   S   G   D   L   G   Q   Q 780                                       790                                       800                                       810                                       820                                       830
ATC TTA GTG CCC ACC AAC CAA GTT GTT CAA GCT GTT GTT CAA GTT ATG GAC GTA CAA ACA TAC
TAG AAT CAC GGG TGG TTG GTT CAA CAA GTT CGA CAA CAA GTT CAA TAC CTG CAT GTT TGT ATG
 I   L   V   P   T   N   Q   V   V   Q   A   V   V   Q   V   M   D   V   Q   T   Y 840                                       850                                       860                                       870                                       880                                       890
CAG ATT CGC ACA GCA CCC ACT AGC ACT ATT GCC CCT GGA GTT GTT ATG TAC TCC TCC CCA
GTC TAA GCG TGT CGT GGG TGA TCG TGA TAA CGG GGA CCT CAA CAA TAC ATG AGG AGG GGT
 Q   I   R   T   A   P   S   T   I   A   P   G   V   V   M   Y   S   S   P
```

```
900                              910                              920                              930                              940                              950
GCA CTT CCT ACA CAG CCT GAA GAA CTT GCT GAA GCA CCA CGA AAG AGA GAG GTC CGT CTA ATG AAG
CGT GAA GGA TGT GTC GGA CTT CGA GCT CGT CTC TCT CAG GCA GAT TAC TTC
 A   L   P   T   Q   P   A   E   E   A   A   R   K   R   E   V   R   L   M   K
                                                 |---------- Basic Region----------

960                              970                              980                              990                              1000                             1010
AAC AGG GAA GCA GCA GCT CGA GAG TGT CGT CGA GAG ACA TCT TTC AGA GAA AAG AAG TAT GTG TTA GAA
TTG TCC CTT CGT CGT CGA GCT CTC ACA GCA GCT CTC TTT CTT ATA CAC ACA AAT CTT
 N   R   E   A   A   R   E   C   R   R   E   T   S   F   R   E   K   K   Y   V   Ⓛ   E─
 |─────────────────

1020                             1030                             1040                             1050                             1060                             1070
AAC AGA GTG CTT GTG CTT GAA AAT CAA CTT TTA GTT TTG TTC TGT AAC TTG ATT GAG GAG CTA AAA GCA CTT
TTG TCT CAC CGT GAC GAC CTT TTA AAT CAA AAC AAG ACA AAC CTC TAA CTC CTC GAT TTT CGT GAA
 N   R   V   A   Ⓛ   E   N   Q   N   K   T   Ⓛ   I   E   E   L   K   A   Ⓛ
                ──────────── Leucine Zipper──────────

1080                             1090                             1100                             1110                             1120                             1130
AAG GAC CTT TAC TGC CAC GTG CTT GAA AAA TCA GAT T AAT TTG GGA TTT AAA TTT TCA CCT GTT AAC
TTC CTG GAA ATG ACG GTG CAC CGT AGT TTT AGT CTA A TTA AAC CCT AAA TTT AAA AGT GGA CAA TTC
 K   D   L   Y   C   H   V   L   E   K   S   D─

1140                             1150                             1160                             1170                             1180                             1190
GTG GAA AAT GGA CTG GCT GGA ACC CGA CCA CAA GGT GTT TCT CAA AGA CAA AAT AAA CAT TTT ATT TTC TAA
CAC CTT TTA CCT GAC CGA TTA CCT CAA AGA GTT TCT CAA CTT TCT TGT GTT TTA TTT GTA AAA TAA AAG ATT 1200                             1210                             1220                             1230                             1240                             1250
ACA TTT CTT TTC TTC TAT GCG CAA AAC TGC ACG GTT TTG CTG AAA GCA ACT ACA GAA TTT CAT TCA TTT
TGT AAA GAA AAG ATA CGC GTT TTG ACG TGC CAA AAC GAC TTT CGT TGA TGT CTT AAA GTA ACT AAA 1260                             1270                             1280                             1290                             1300                             1310
GTG CTT TTG CAT TAA ACT GTG AAT GTT CCA ACA CCT GCC TCC ACT TCT CCC CTC AAG AAA
CAC GAA AAC GTA ATT TGA CAC TTA CAA GGT TGT GGA CGG AGG TGA ACA GGG CAG TTC TTT 1320                             1330                             1340                             1350                             1360                             1370
TTT TCA ACG TGC GGA ATC ATG AAG AGA CTT CTG CTT TTC AAC CCC CAC GTG CCT CCT CAA GAA
AAA AGT ACG CCT TAG TAC TTC TCT GAA GAC GAA GAA AAG TTG GGG GTG GGA GGA GTT CTT
```

FIG. 1D

```
1380                        1390                        1400                        1410                        1420                        1430
GTA ATA ATT TGT TTA CTT GTA AAT TGA TGG GAG AAA TGA GGA AAA GAA AAT CTT TTT AAA
CAT TAT TAA ACA AAT GAA CAT TTA ACT ACC CTC TTT ACT CCT TTA GAA AAA TTT 1440                        1450                        1460                        1470                        1480                        1490
AAT GAT TTC AAG GTT TGT GCT GAG CTC CTT GAT TGC CTT AGG GAC AGA ATT ACC CCA GCC
TTA CTA AAG TTC CAA GTA ACA CGA CTC GAA CTA ACG TCC CTG TCT TAA TGG GGT CGG 1500                        1510                        1520                        1530                        1540                        1550
TCT TGA GCT GAA GTA ATG TGT GGG CCG CAT GCA TAA AGT AAG TAA GGT GCA ATG AAG AAG
ACA ACT CCA CTT CAT TAC ACA CCC GGC GTA CGT ATT TCA TTC ATT CCA TAC TTC TTC 1560                        1570                        1580                        1590                        1600                        1610
TGT TGA CCA AAT TGA CAT GTT GTC ACA TTC TCA TTG TGA ATT ATG TAA AGT TGT TAA
ACA ACT AAC GGT TTA ACT GTA CAA CAG TGT AAG AGT AAC ACT TAA TAC ATT TCA ACA ATT 1620                        1630                        1640                        1650                        1660                        1670
GAG ACA TAC CCT CTA AAA AAG AAC TTT AGC ATG GTA TTG AAG GAA TTA GAA ATG AAT TTG
CTC TGT ATG GGA GAT TTT TTC TTG AAA TCG TAC CAT AAC TTC CTT AAT CTT TAC TTA AAC 1680                        1690                        1700                        1710                        1720                        1730
CAG TGC TTT TTA TGT ATG TTG TCT TCT TCA ATA CTG AAA ATT TGT CCT TGG TTC TTA AAA
CTC ACG AAA AAT ACA TAC AAC AGA AGA AGT TAT GAC TTT AAC ACA GGA ACC AAG AAT TTT 1740                        1750                        1760                        1770                        1780                        1790
GCA TTC TGT ACT AAT ACA GCT CTT CCA TAG GGC AGT TGT TTC TTA ATT CAG TTC TGT
CGT AAG ACA TGA TTA TGT CGA GAA GGT ATC CCG TCA ACA AAG AAT TAA GTC AAG ACA 1800                        1810                        1820                        1830                        1840                        1850
ATG TGT TCA ACA TTT TTG AAT ACA TTA AAA GTA AAA GTA ACC TGA ACC AAG CAT GGT
TAC ACA ACT TGT AAA AAC TTA TGT AAT TTT CTT CAT TTT CAT TGG TTG ACT TGC GTA CCA 1860                        1870                        1880                        1890                        1900                        1910
ATT TGA ATT TTA AAT TAA ATT GTA AAT AAA AGT ACA AAG CAT ATT TTA GTT AGT ACT
TAA ACT TAA ATT TCG TTT CAT TTA TTT TCA TGT TTC GTA TAA AAT CAA TCA TGA 1920                        1930                        1940                        1950                        1960                        1970
AAA TTC TTA GTA AAA TGC TGA AAC CAA GTA TCC CTT GAG TTA TAT AAC AAG ATT TTT
TTT AAG AAT CAT TTT ACG ACT AGT CAT TTG GTT AGG GAA CTC AAT ATA TTG TTC TAA AAA
```

```
1980                              1990                              2000                              2010                              2020                              2030
AAA TAA ATG TTA TTG TCC TCA CCT TCA AAA ATA TTT ATA TTG TCA CTC ATT TAC GTA AAA
TTT ATT TAC AAT AAC AGG AGT GGA AGT TTT AAA TAT AAC AGT GAG TAA ATG CAT TTT 2040                              2050                              2060                              2070                              2080                              2090
AGA TAT TTC TAA TTT ACT GTT GCC CAT TGC ACT TAC ATA CCA CCA AGA AAG CCT TCA
TCT ATA AAG ATT AAA TGA CAA CGG GTA ACG TGA ATG TAT GGT GGT TCT TTC GGA AGT 2100                              2110                              2120                              2130                              2140                              2150
AGA TGT CAA ATA AAG CAA AGT GAT ATA TAT TTG TTT ATG TAC TGT AAA AAT TTT TTA
TCT ACA GTT TAT TTC GTT TCA CTA TAT ATA AAC AAA TAC TTT ACA ATG TAC ATC TTA 2160                              2170                              2180                              2190                              2200                              2210
ACT GAT TTT AAA TAT TTT CCA TAT TAA CAA TTT AAC AGA TCT CTA GTG AAT TTT TTA
TGA CTA AAA TTT ATA AAA GGT ATA ATT GTT AAA TTG TCT AGA GAT CAC TTA AAA AAT 2220                              2230                              2240                              2250                              2260                              2270
AAT GAA AGA AGT TGT AAG GAT ATA AAA AGT ACA GTG TTA GAT GTG CAC AAG GAA AGT TAT
TTA CTT TCT TCA ACA TTC CTA TAT TTT TCA TGT CAC AAT CTA CAC GTG TTC CTT TCA ATA 2280                              2290                              2300                              2310                              2320                              2330
TTT CAG ACA TAT TTG AAT GAC TGC TGT ACT AGT TAT TAG TTC TCA TTG TCA TTC TTA CAA AAC
AAA GTC TGT ATA AAC TTA CTG ACG ACA TGA CGT TCA ATA ATC AAG CCT AAC AGT AAG AAT GTT TTG 2340                              2350                              2360                              2370                              2380                              2390
ATT TTT TTC TCT TCT AAA AAC ACT AGT TAT TAG TTC TGC TTT AGC TTT CCA ATA TGC
TAA AAA AAG ACA AGA TTT TTG TCA ATA ATC AAG ACG AAA TCG AAA GGT TAT ACG 2400                              2410                              2420                              2430                              2440                              2450
TGT ATA GCC TTT GTC ATT TTA TAA TTT TAA TTC CTG ATT AAA ACA GTC TGT ATT TGT GTA
ACA TAT CGG AAA CAG TAA AAT ATT AAA ATT AAG GAC TAA TTT TGT CAG TAA ACA CAT 2460                              2470
TAT CAT CCC CCC GAA TTC
ATA GTA GGG GGG CTT AAG (SEQ. ID. NO.5 )
```

FIG. 1E

| | | |
|---|---|---|
| CREB | LENRVAVLENQNKTLIEELKALRTFTA | (SEQ. ID. NO. 6) |
| C/EBP | LTSDNDRLRKRVEQLSRELDTLRGIFR | (SEQ. ID. NO. 7) |
| C-JUN | LEEKVKTLKAQNSELASTANMLREQVA | (SEQ. ID. NO. 8) |
| GCN4 | LEDKVEELLSKNYHLENEVARLKKLVG | (SEQ. ID. NO. 9) |
| V-FOS | LQAETDQLEDKKSALQTEIANLLKEKE | (SEQ. ID. NO.10) |
| human n-myc | LQAEEHQLLLEKEKLQARQQQLLKKIE | (SEQ. ID. NO.11) |
| human L-myc | LVGAEKRMATEKRQLRCRQQQLQKRIA | (SEQ. ID. NO.12) |
| mouse c-myc | LTSEKDLLRKRREQLKHKLEQLRNSGA | (SEQ. ID. NO.13) |

FIG. 3

```
            262
CREB    TQPAEEAAR KR EV R LMKNR E
C-JUN   IDMESQERI KA ER KR MRNR I
        245
                                    ↓
CREB    AA RE CRRKK KE YVKC LE N RV
C-JUN   AA SK CRKRK LE RIAR LE E KV
         ↓              ↓        ↓
                                        321
CREB    AV LE NQ N KT L I EELKA LK D L (SEQ. ID. NO. 6)
C-JUN   KT L KA QN SE L ASTANM LR EQ (SEQ. ID. NO. 14)
                                        304
```

FIG. 4

CAMP-RESPONSIVE TRANSCRIPTIONAL ENHANCER BINDING PROTEIN

CROSS-REFERENCE TO RELATED APPLICATIONS

This application is a 371 of PCT/US89/05234, filed Nov. 20, 1989 and is a continuation-in-part of U.S. application Ser. No. 07/272,980, filed Nov. 18, 1998, now abandoned, the contents of which are fully incorporated herein by reference.

The research underlying this patent application was supported by National Institutes of Health Grant DK-25532; the government has certain rights in this invention.

FIELD OF THE INVENTION

This invention is in the field of genetic engineering, specifically directed toward the characterization and cloning of a cAMP-responsive transcription enhancer binding protein (CREB). The invention is also directed to methods for the use of the CREB protein to increase or decrease the production of specific proteins in eukaryotic cells by activating transcription of a recombinant gene in response to cAMP.

BACKGROUND OF THE INVENTION

Within the cell, transcriptional selectivity of eukaryotic genes is mediated by complex control regions composed of different combinations of promoter and enhancer elements. These regions are arrayed in tandem to allow multiple distinct regulatory factors to function coordinately to potentiate RNA synthesis. This mosaic arrangement of eukaryotic transcriptional regulatory elements provides different genes with the possibility of utilizing some of the same regulatory elements.

Enhancers are sequence-specific DNA transcriptional regulatory elements that function in cis to stimulate the transcription of genes placed in proximity to them. Generally, elements that function in cis are recognition sites for cellular proteins (Dynan, W. S. et al., *Nature* 316:774–778 (1985)). The cellular proteins which recognize enhancer sequences are often expressed in a manner which is tissue-specific or species-specific, or dependent upon the hormonal environment. Upon binding of the appropriate protein to the enhancer region, transcription of genes under the control of, that is, operably-linked to the enhancer is facilitated, resulting in an increased transcriptional expression of the gene, and thus in an increased expression of any protein for which the gene codes.

Enhancers are not orientation dependent elements like promoter regions are. Enhancer sequences can be oriented in either direction relative to the direction of transcription of the operably-linked gene. In addition, the sequence itself may be located anywhere in the general area of the gene, such as 5' to the promoter region, 3' to the transcriptional termination site, or even within a transcribed region of the gene, for example, in an intron. A gene may be under the transcriptional regulatory influence of multiple copies of the same enhancer, or the gene may be under the transcriptional regulatory influence of a group of different enhancers, each enhancer in the group conferring a different regulatory response on the operably-linked gene. Examples of these responses include an ability to transcriptionally respond to different agents or hormones, and tissue-specific expression of the gene.

Because of their relative orientation independence, enhancers can be located at varying distances from the promoter and transcription unit of the gene and yet still be operably-linked to that gene. The transcription unit is that sequence of a gene which is transcribed. The distance will vary with the transcriptional strength of the promoter and enhancer. Typically, on the average, enhancers are located within 200 bases upstream from the promoter site which itself determines the base at which transcription begins.

Cyclic adenosine monophosphate (cAMP) is the intracellular second messenger for many hormones or biological mediators and is known to be active in the regulation of gene expression in both prokaryotes and eukaryotes. In eukaryotes, the regulation of transcription by cAMP has been extensively studied in animals and tissue culture cells. Increasing the intracellular cAMP concentration with hormones such as glucagon or other agents such as cAMP analogs or beta-adrenergic agonists induces the transcription of many genes in a tissue-specific manner, including somatostatin (Montminy, M. R. et al., *Proc. Natl. Acad. Sci. USA* 83:6682 (1986)), the alpha subunit of human chorionic gonadotropin (Silver, B. J. et al., *Proc. Natl. Acad. Sci. USA* 84:2198 (1987); Jameson, J. L. et al., *Endocrinology* 119:2570 (1986); Delegeane, A. M. et al., *Mol. Cell. Biol.* 7:3994 (1987); Jameson, J. L. et al., *Mol. and Cell. Biol.* 7:3032 (1987); Deutsch, P. J. et al., *Bio. Chem.* 262:12169 (1987)); phosphoenolpyruvate carboxykinase (Short, J. M. et al., *Biol. Chem.* 261:9721–9726 (1986)), tyrosine hydroxylase (Lewis, E. J. et al., *Proc. Natl. Acad. Sci. USA* 84:3550–3554 (1987)), and c-fos (Greenberg, M. E. et al., *J. Biol. Chem.* 160:14101–14110 (1985)).

Cyclic AMP-responsive genes contain a sequence homologous to the sequence TGACGTCA located on the 5' side of their mRNA cap sites. This sequence has been termed a cAMP-responsive enhancer element (CRE). Deletion mutagenesis of cAMP-inducible genes has shown that the cAMP-responsive enhancer element is contained within a domain necessary for cAMP-mediated induction of tranttscription.

Similar consensus DNA regulatory elements involved in the stimulation of gene transcription have been identified for other molecules, such as for the tumor promoter 12-0-tetradecanoylphorbol-13-acetate (TPA) (Imbra, R. J. et al., *Mol. and Cell. Bio.* 7:1358 (1987); Angel, P. et al., *Cell* 49:729 (1987); Tsukada, T. et al., *Bio. Chem.* 262:8743 (1987); Angel, P. et al., *Mol. and Cell. Biol.* 6:1760 (1986); Chiu, R. et al., *Nature* 329:648 (1987); Angel s P. et al. *Mol. and Cell. Biol.* 74:2256 (1987); Comb, M. et al., *Nature* 323:353 (1986)). However, notably, the sequence of the octameric cAMP-response element, CRE, (5'-TGACGTCA-3') differs from that of the heptameric TPA-response element, TRE, (5'-TGAGTCA-3') by a single base.

Early studies suggested that transcriptional stimulation by both cAMP and TPA was mediated through a common DNA sequence present in the 5' regulatory region of the enkephalin gene, 5'-TGCGTCA-3'(Comb, M. et al., *Nature* 323:353 (1986)). However, a DNA binding protein of 47 Kd (AP-1 or c-jun) was isolated and shown to mediate TPA but not cAMP induction of SV40 gene transcription through a mechanism involving sequence-specific binding to the TRE motif (Lee, W. et al., *Cell* 49:741 (1987)). Similarly, a 43 Kd protein termed CRE-binding protein (CREB) has been identified that binds to a CRE sequence in the 5' regulatory region of the rat somatostatin gene (Montminy, M. R. et al., *Nature* 328:175 (1987)). In placental JEG-3 cells, a 38 Kd protein was shown to bind to CRE (Deutsch, P. J., et al., *Proc. Natl. Acad. Sci. USA* 85:7922 (1988)). However, the sequence of CREB had not previously been determined, precluding the undertaking of detailed structural or functional studies.

Anti-sense RNA refers to RNA synthesized with a sequence complementary to that found in a specific mRNA. Anti-sense RNA has been used to inhibit, in a specific manner, the expression of the protein whose mRNA is being hybridized by the anti-sense RNA. Inhibition by hybridization in eukaryotes is thought to occur at the level of processing of the mRNA (thus preventing its translocation to the cytoplasm) while in prokaryotes it is thought to occur at translation of the mRNA. At either step, the ultimate result is to effectively stop expression of the target protein whether the system is bacteria, plants or other eukaryotic systems (Knecht, D. A. et al., Science 236:1081–1086 (1987); Van Der Krol, A. R. et al., Nature 333:866–869 (1988); Cabrera, C. V. et al., Cell 50:659–663 (1987); Boulay, J. L. et al., Nature 330:395–398 (1987); Rothstein, S. J. et al;, Proc. Natl. Acad. Sci. USA 84:8439–8443 (1987); Ecker, J. R. et al., Proc. Natl. Acad. Sci. USA 83:5372–5376 (1986); Lichtenstein, D., Nature 333:801–802 (1988)). However, it has not previously been known to use cAMP with anti-sense RNA technology to control the expression of specific proteins in a manner capable of acute regulation in response to the levels of cAMP in the system.

SUMMARY OF THE INVENTION

This invention is directed toward the characterization and cloning of DNA encoding a cAMP-responsive transcription enhancer binding protein (CREB) and the recombinant protein produced by this DNA. This protein, CREB, is a DNA binding protein and is capable of recognizing and binding to DNA containing the cAMP enhancer element, CRE, and selectively activating transcription of genes operably-linked to the enhancer element in eukaryotic cells. The present invention also provides methods for the selective stimulation of transcription of recombinant genes using the CREB protein. Especially, the present invention provides methods for the selective stimulation of transcription of recombinant genes using the CREB protein in response to cAMP. The present invention further provides methods for the selective inhibition of protein expression using the CREB protein of the invention and cAMP to stimulate the synthesis of an anti-sense RNA. The methods of the invention allow, for the first time, the acute regulation of specific protein levels, in both a positive and negative manner using cAMP or hormones or other agents which act through cAMP to enhance transcription.

DESCRIPTION OF THE FIGURES

FIG. 1. Primary structure of CREB.

The basic region and leucine zipper sequence located at the carboxyl terminus of the protein are underlined. The periodic array of leucine residues (circled) spaced seven residues apart would form the hypothetical alpha helix involved in protein-protein contacts (Landschultz, W. H. et al., Science 240:1760 (1988)). Preliminary evidence indicates that the methionine at a position one is the translational start site in vivo. Amino acid sequence is in single letter code.

Figure 2:
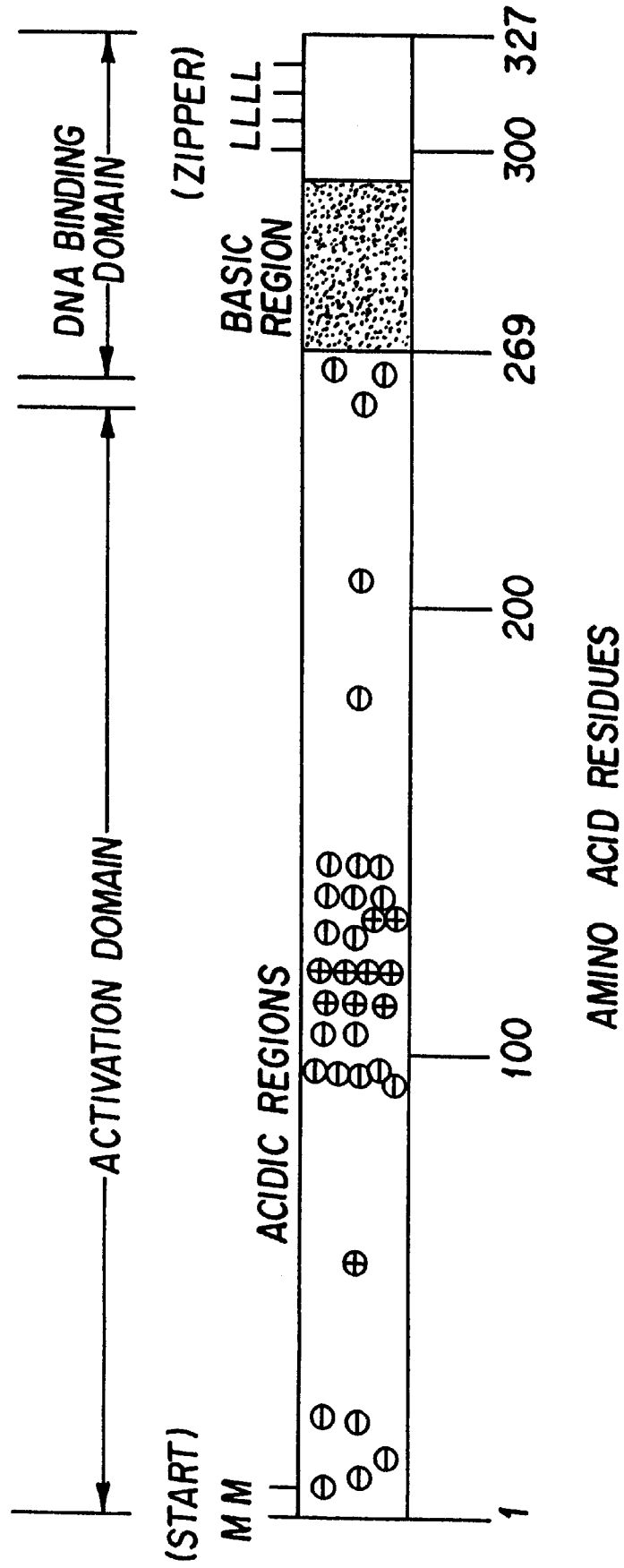

FIG. 2. Diagram of the hypothetical functional domains of CREB.

Basic region and leucine zipper sequence at the carboxyl terminus provide the putative DNA binding domain. The amino terminal residues 1–268 constitute the proposed negatively charged activation domain in which 25 of the 36 charged amino acids (exclusive of the two histidine residues) are glutamic and aspartic acids. This region of the protein has characteristics of a "negative noodle" hypothesized to be involved in the coupling of DNA binding proteins to other transcriptional factors (Sigler, P. S., Nature 333:210 (1988); Hope, I. A. et al., Nature 333:635 (1988); Ma, J. et al., Cell 48:847 (1987); and Gill, G. et al., Cell 51:121 (1987)).

FIG. 3. Comparisons of leucine zipper regions in the structure of CREB and other DNA binding proteins.

Alignment of leucine zipper regions of CREB and several other proteins. Leucines reside at every seventh position, a periodicity required for hypothetical alignment of the leucines on the same spoke of an idealized alpha helix.

FIG. 4. Comparison of sequence similarities between CREB and c-jun.

A region of primary sequence similarity between CREB and c-jun is localized to the basic region that is adjacent to the leucine zipper region. Boxed residues are shared by the two DNA binding proteins. Arginine and lysine are considered interchangeable. Arrows point to leucines in the zipper region. Sequence positions numbered correspond to those of CREB, FIG. 2, and c-jun (Bohmann, D. et al., Science 238:1386 (1987); and Angel, P. et al., Nature 332:166 (1988)).

Figure 5:
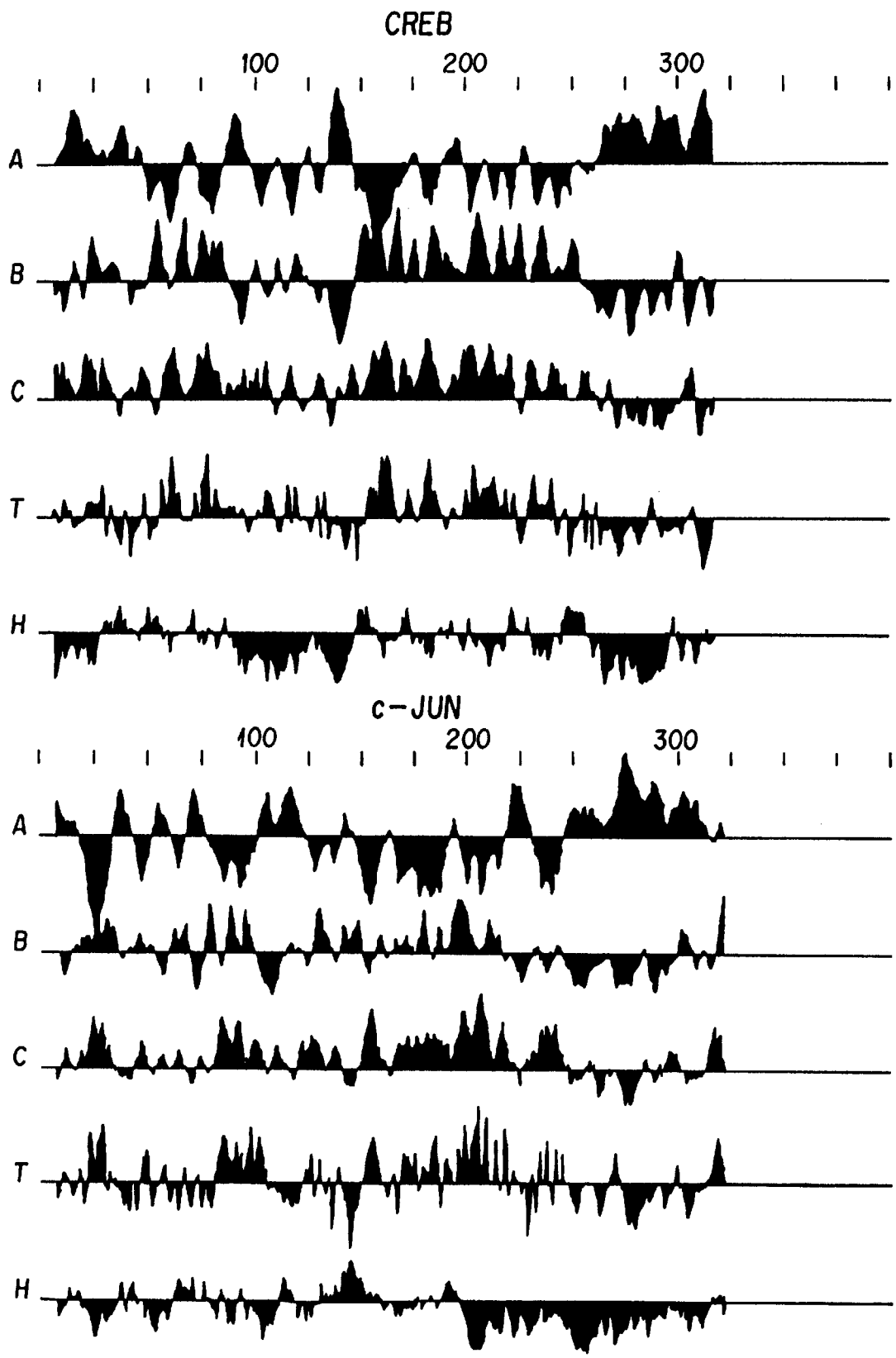

FIG. 5. Secondary structure comparisons of CREB and c-jun.

The plots compare four parameters of secondary structures: alpha helix (A), beta strand (B), random coil (C), beta turn (T), as well as hydrophobicities (H) (Garnier, J. et al., J. Mol. Biol. 120:97 (1978); and Kyte, J. et al., J. Mol. Biol. 157:105 (1982)) (MacGene Plus computer program). Numbers at top refer to the sequence of CREB (326 residues) and c-jun (331 residues). Note overall similarities in the secondary structures of the two proteins despite notable absence of similarities of the primary amino acid sequence as seen in FIG. 1 between CREB and c-jun as cited in Bohmann, D., et al., Science 238:1386 (1987) and Angel, P., et al., Nature 332:166 (1988).

DEFINITIONS

In order to provide a clear and consistent understanding of the specification and claims, including the scope to be given such terms, the following definitions are provided.

Selectively activate transcription. To "selectively activate transcription" means to activate or increase the transcription of a heterologous gene or group of genes, without activating transcription in general.

Selectively inhibit expression. To "selectively inhibit expression of a protein means to inhibit, decrease or stop the expression, transcription, mRNA processing, translation or synthesis of a specific protein or group of proteins, either endogenous or heterologous, without inhibiting the ability of the cell to express, transcribe, process, translate or synthesize proteins in general.

DNA element. A "DNA element" is a DNA sequence which confers a unique property on a gene which is operably-linked to it. DNA elements include enhancer sequences and may confer hormonal responsiveness or tissue-specific expression on a gene.

Minimal selectable region. The term "minimal selectable region" refers to an isolatable DNA region or sequence containing the sequence information required to confer a unique function or other property on a DNA construct which contains the minimal selectable region. Examples of minimal selectable regions are a promoter sequence, the CREB sequence, the CRE enhancer element, a heterologous gene, transcriptional stop sites, and the like.

Operably-linked. By "operably-linked" is meant that a DNA element or minimal selectable region is located at a site which places a gene or group of genes under the control or influence of that element or region. For example, an operably-linked promoter sequence is the promoter for the gene; an operably-linked enhancer sequence is capable of enhancing the transcription of genes operably-linked to it.

DETAILED DESCRIPTION OF THE INVENTION

Cyclic AMP is an intracellular second messenger that activates transcription of many cellular genes. A cAMP-responsive transcriptional element (CRE) has been identified as a palindromic consensus DNA sequence, TGACGTCA. This sequence functions as a DNA enhancer specific for cAMP regulatory events. Although the CRE is a component of the regulatory region of cAMP-responsive genes, the presence of this sequence is not itself sufficient for cAMP inducibility. Exposure of the cell to stimuli that increase cAMP is necessary to stimulate a cascade of events which ultimately produces a transcriptionally active (or activated) complex between the CRE element and a specific transcriptional factor which binds to this element. According to this invention, the transcriptional factor has now been characterized and cloned. This transcriptional factor is a unique CRE-binding protein, abbreviated CREB. CREB is a DNA binding protein which specifically responds to cAMP-induced regulatory events by binding DNA that contains the CRE enhancer element and stimulating transcription. The CREB protein of the invention can be used to regulate the transcription of recombinant genes that have been operably-linked to the CRE enhancer. Such constructs can be used to increase or decrease the expression of specific proteins in a cAMP-dependent manner.

The DNA encoding CREB of the invention was found by screening a placental λ gt11 library for expression of specific CRE-recognition and binding proteins using the CRE sequence as a radioactive probe. A cDNA encoding a protein of 326 amino acids with the binding properties of a specific CRE-recognition and binding protein (CREB) was isolated. The CREB protein encoded by the isolated DNA contains a carboxy terminal basic region adjacent to a leucine zipper sequence which is similar to sequences believed to be involved in DNA binding and in protein-protein contacts in several other DNA-associated transcriptional proteins, including c-myc, c-fos, c-jun and GCN4. CREB also contains an amino terminal acidic region proposed to be a potential transcriptional activation domain. The putative DNA binding domain of CREB is structurally similar to the corresponding domains in the phorbol ester-responsive proto-oncogene c-jun and the yeast transcription factor GCN4 that bind to a heptameric DNA element, TGAGTCA, closely related to the CRE octamer.

Based upon the deduced protein sequence of this cloned cDNA, the cDNA encodes a full-length CREB protein with a calculated molecular mass of 35,024 daltons. This conclusion is consistent with the finding of a 38 Kd CREB protein present in extracts of JEG-3. human choriocarcinoma cells, assuming that the cellular protein is post-translationally modified. The apparent discrepancy in molecular weights between this human placental CREB of 38 Kd and the 43 Kd CREB identified in rat adrenal cells (PC-12) by Montminy and Bilzikjian (Montminy, M. R. et al., *Nature* 328:175 (1987)) could be due to species-specific differences in primary structure, post-translational modifications, or the existence of multiple CREB proteins which are part of a larger family of CREB transcriptional activators. Recent reports have suggested that a 45 Kd E1A-regulated cellular transcription factor (ATF) is similar or identical to CREB and that ATF/CREB can be regulated in vivo by both the adenovirus E1A protein and cAMP (Lin, Y-S. et al., *Proc. Natl. Acad. Sci. USA* 85:3396 (1988); and Hardy, S. et al., *Proc. Natl. Acad. Sci. USA* 85:4171 (1988)).

Isolation of the cDNA encoding CREB will facilitate studies aimed at addressing the basis for the molecular heterogeneity of CREB and CREB-like proteins and the interactions of CREB-like, fos-related, and jun-related proteins in the transcriptional activation of genes.

In addition a recombinant source of CREB will greatly facilitate studies directed towards elucidating the mechanisms through which cAMP modulates intracellular metabolism by directing transcriptional events. Genes suspected of being under cAMP control can be evaluated in terms of their ability to respond to, or bind, the CREB of the invention. Recombinant CREB will also facilitate studies directed towards elucidating the transcriptional mechanism-of-action of hormones and other agents suspected of acting through cAMP by examining their ability to influence CREB-directed transcription.

Further, since CREB is a transcriptional activator which activates transcription of genes operably-linked to the CRE element in eukaryotic cells, according to the methods of this invention, CREB can be used in conjunction with CRE and especially with cAMP to increase production of heterologous proteins and polypeptides by stimulating expression of recombinant genes. The CREB protein of the invention can also be used to activate the transcription of an RNA sequence which is not translated, such as an RNA sequence complementary to a known mRNA, or anti-sense RNA. Expression of an anti-sense RNA can be used to block the expression of endogenous or heterologous proteins.

Lastly, the CREB-CRE transcription methods of the invention provide methods of cAMP-controlled mutagenesis in eukaryotic cells.

Thus, the invention encompasses any construct or set of constructs which relies on CREB and CRE recognition or binding to alter the expression of a homologous or heterologous gene product by enhancing the transcription of a recombinant RNA.

The preferred hosts are mammalian cells, grown in vitro in tissue culture, or in vivo in animals. Mammalian cells provide post translational modifications to proteins and polypeptides including correct folding or glycosylation at correct sites.

Mammalian cells which may be useful as hosts include cells of fibroblast origin such as VERO or Chinese hamster ovary CHO-K1, or cells of lymphoid origin, such as the hybridoma SP2/O-AG14 or the myeloma P3×63Sg8, and their derivatives. Preferred mammalian host cells include SP2/O and J558L. In one preferred embodiment the CREB sequence of the invention is provided to the host cell in a transcribable and translatable minimal selectable region on the same vector construct as that providing the CRE minimal selectable region operably-linked to a recombinant gene. In another preferred embodiment, the CREB sequence of the invention is provided to the host cell in a transcribable and translatable minimal selectable region on a vector construct which is separate and maintained as a separate replicating unit from that providing the CRE minimal selectable region operably-linked to a recombinant gene.

The CREB-encoding DNA of the invention, in an expressible form, can also be inserted into the chromosome of the host cell. CREB functions in trans which means that it is the diffusible product of the CREB gene which functionally activates expression of genes operably-linked to the CRE element in response to cAMP. Therefore, it is necessary only that the minimal selectable region bearing the CREB gene of the invention be present in the same cell as the minimal selectable region providing the CRE element; the CREB DNA sequence need not be physically linked to the plasmid or element bearing the CRE sequence.

The CREB protein as depicted in FIG. 1, or active CRE recognition and binding fragments thereof, may be used in the method of this invention in several embodiments. It is to be understood that while the full octameric CRE sequence is necessary to the construct, it is not necessary that the full-length CREB sequence be used. Only the portion of the CREB sequence necessary to functionally activate transcription and recognize and bind to DNA containing the CRE sequence is needed. Active CRE recognition and binding fragments may be determined by routine screening. Further, FIG. 2 provides a diagram of the proposed functional domains of CREB.

It is also to be understood that by using techniques known to those of ordinary skill in the art it is possible to design chimeric constructs of the CREB protein which contain the ability to recognize the CRE element and thus respond to cAMP in a highly specific manner but which bind to or activate different targets in DNA. Such a chimeric construct might ligate the amino-terminal portion of the CREB protein of the invention with the DNA binding and "zipper" region from another DNA binding protein, or, place the DNA binding and zipper portion of the CREB protein with an alternate amino-terminal domain thus altering the transcriptional targets of the cAMP response.

The promoter chosen to regulate expression of the CREB protein of the invention may be the same or different from the promoter chosen to regulate the recombinant gene. In one embodiment, no enhancer is operably-linked to the promoter operably-linked to CREB. In a preferred embodiment, the CRE element is operably-linked to the CREB promoter so that CREB synthesis enhances its own transcription and expression. In another embodiment, enhancers conferring tissue or species specificity, such as GCN4 in yeast, are operably-linked to the CREB promoter, which may or may not be operably-linked to CRE also. Any promoter capable of directing the RNA polymerase II transcription of the operably-linked recombinant CREB gene is applicable to the methods of the invention. RNA polymerase II is that RNA polymerase which specifically transcribes DNA into mRNA. Promoter selection is important only in that it allows the host cell to express enough of the CREB protein of the invention so that the level of CREB protein is not a factor limiting the stimulation of the CRE-recombinant gene construct.

In one embodiment the promoter used for the CREB construct of the invention is the homologous CREB promoter from the human placenta. In another embodiment, the CREB promoter from the tissue or cell line of interest is used. Because CREB should not be in limiting quantities it is desirable that a strong promoter be used. By strong promoter is meant a promoter possessing a high affinity for RNA polymerase, as one which provides an accessible RNA polymerase entry site. Examples of strong eukaryotic promoters include promoters from SV40, actin, Rous sarcoma virus, herpes virus, thymidine kinase, and adenovirus MLTV.

The CREB construct as shown in FIG. 1 provides the translational stop and start sites and capping site necessary for the proper translation of the sequence into a functional CREB protein in eukaryotic systems.

For a mammalian host, several possible vector systems are available for the expression of either or both the CREB protein of the invention and the heterologous recombinant protein. One class of vectors utilizes DNA elements which provide autonomously replicating extra-chromosomal plasmids, derived from animal viruses such as bovine papilloma virus, polyomavirus, adenovirus, or SV40 virus. A second class of vectors relies upon the integration of the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g. antibiotics, or heavy metals, such as copper, or the like. The selectable marker gene can either be directly linked to the DNA gene sequences to be expressed, or introduced into the same cell by co-transfection. Preferably the marker is a dominant-acting marker which produces a discernable change in the phenotype of normal cells. Colbere-Garapin, F. et al., *J. Mol. Biol.* 150:1 (1980).

The constructs may be introduced into a host cell by transformation in conjunction with a gene allowing for selection where the construct will become integrated into the host genome. Usually the construct will be part of a vector having a replication system recognized by the host cell. In another embodiment of this invention, the host cell has been modified prior to transformation with the construct containing the CRE and the heterologous gene so that the cell is already actively expressing the CREB protein, or active CRE recognition and binding fragments, or, maintains the CREB protein or active CRE recognition and binding fragment integrated in its genome.

When the CREB-encoding DNA of the invention is inserted into the host cell chromosome, DNA amplification techniques can be used to increase the copy number of the CREB gene. Amplification serves the same purpose as a multi-copy plasmid in so far as it results in multiple copies of a functional gene.

Another preferred host is yeast. Yeast provide substantial advantages in that yeast are capable of post-translational peptide modifications including glycosylation (Kukuruzinaka, M. A. et al., *Ann. Rev. Biochem.* 56:915–944 (1987)), and a number of recombinant DNA strategies exist which utilize strong promoter sequences and high copy number plasmids which promote the production of large amounts of the desired protein. Yeast also recognize leader sequences on cloned mammalian gene products, and can secrete peptides bearing leader sequences (i.e., prepeptides). Botstein, D. et al., *Science* 240:1439–1443 (1988); Struhl, K., *Nature* 305:391–397 (1983); Sherman, F. et al., *Methods in Yeast Genetics-Laboratory Manual,* Cold Spring Harbor Laboratory, New York, 1983.

Any of a series of yeast gene expression systems incorporating promoter and termination elements from the actively expressed yeast genes coding for proteins, especially glycolytic enzymes such as phosphoglycerate kinase, glyceraldehyde-3-phosphate dehydrogenase, glucokinase, hexokinase, pyruvate kinase, pyruvate decarboxylate, phosphofructokinase, glucose-6-phosphate isomerase, 3-phosphoglycerate mutase, triosephosphate isomerase, phosphoglucose isomerase, alcohol dehydrogenase, isocytochrome C and the like, produced in large quantities when yeast are grown in medium rich in glucose can be utilized.

See, for example, Broach, J. R., *Meth. Enz.* 101:307 (1983); Stinchcomb et al., *Nature* 282:39 (1979); Tschempe et al., *Gene* 10:157 (1980); and Clark, L., et al., *Meth. Enz.* 101:300 (1983). Known glycolytic genes can also provide very efficient transcription control signals. Hess et al., *J. Adv. Enzyme Reg.* 7:149 (1968); Hitzeman et al., *J. Biol. Chem.* 255:2073 (1980); and Holland, M. J., *J. Biol. Chem.* 256:1385 (1981).

Another preferred host is insect cells, for example the Drosophila larvae. Using insect cells as hosts, the Drosophila alcohol dehydrogenase promoter can be used. Rubin, G. M., *Science* 240:1453–1459 (1988). Alternatively, baculovirus vectors can be engineered to express large amounts of protein in insects (Jasny, B. R., *Science* 238:1653 (1987); Miller, D. W., et al., in *Genetic Engineering* (1986), Setlow, J. K., et al., eds., *Plenum*, Vol. 8, pp. 277–297).

To express a heterologous protein in the method according to this invention, transcriptional and translational eukaryotic signals recognized by the eukaryotic host are necessary. Expression vehicles for production of heterologous protein include plasmids or other vectors as described for the CREB protein of the invention. The vector chosen to carry the CREB minimal selectable region and the vector chosen to carry the minimal selectable region containing the CRE element operably-linked to a heterologous recombinant gene, must also contain replicon and control sequences which are derived from species compatible with the host cell and used in connection with the host. The vector ordinarily carries a replicon site, as well as specific genes which are capable of providing phenotypic selection in transformed cells.

The DNA sequence coding for the heterologous protein may be obtained in association with its homologous promoter region from genomic DNA. To the extent that the host cells recognize the transcriptional and translational regulatory signals and the mRNA processing signals associated with the heterologous protein's gene, then the regions 5' or 3' to the heterologous protein's transcribed coding sequence and the introns may be retained and employed for transcriptional and translational processing and regulation.

In another embodiment the minimal selectable region containing the recombinant gene construct operably links a homologous promoter region for the recombinant gene or a heterologous promoter to a recombinant gene containing no introns.

According to the methods of the invention, stimulation of transcription in response to cAMP can be used in combination with other transcriptional and translational regulatory sequences. Other transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated.

The contiguous non-coding region 5' to the heterologous protein which is retained after processing the introns out of the mRNA precursor will normally include those sequences involved with initiation of transcription and translation, such as the TATA box, capping sequence, CAAT sequence, and the like. Usually the 5'-non-coding sequence will be at least 150 bp, more usually at least 200 bp, usually not exceeding about 2 kbp, more usually not exceeding about 1 kbp.

The non-coding region 3' to the heterologous protein coding sequence in the native gene may be retained for its transcriptional termination regulatory sequences, such as termination and polyadenylation. Thus, by retaining the 3'-region naturally contiguous to the DNA sequence coding for the translated region, the transcriptional termination signals may be provided. Where the transcriptional termination signals are not satisfactorily functional in the expression host cell, then a 3' untranslated region functional in the host cell may be substituted with the 3' region of a highly transcribed protein. In this method, the choice of protein for the substituted 3' region would depend on the cell system chosen for production.

The construct for the heterologous protein will comprise the CRE sequence. CRE is a palindrome, which is a bilaterally symmetrical DNA sequence which, therefore, reads the same in both directions. In the methods according to this invention, to express a protein, a construct is made which contains minimal selectable regions comprising a CRE element operably-linked to a promoter which is operably-linked to a heterologous gene. The orientation of the CRE sequence of the invention can be either 5' or 3' relative to the direction of transcription of the recombinant gene. The CRE element may be located either 5' to 3' to, or within the transcriptional unit itself. By transcriptional unit is meant the DNA sequence that is transcribed into RNA.

More than one CRE sequence may be inserted into the construct and operably-linked to the promoter of the heterologous gene if the addition of additional CRE elements does not detrimentally alter the ability of cAMP to stimulate transcription of the gene. In addition, CRE elements may be separated by DNA spacers of variable length and sequences so long as those spacer regions are not detrimental to the ability of the CREB protein to recognize, bind and stimulate the transcription of the heterologous gene.

Once the vectors or minimal selectable regions containing the constructs have been prepared for expression, they may be introduced into the appropriate host. Various techniques may be employed to transform the host with the vectors or constructs, such as protoplast fusion, calcium phosphate-precipitation, electroporation, viral infection or other conventional techniques. After the transformation or transfection, the cells are grown in a selective medium, where untransformed cells are killed, leaving only cells transformed with the constructs of the invention.

Expression of the heterologous gene(s) is stimulated by the addition of cAMP or, by the addition of any analog or hormone acting through cAMP to which the cell is responsive, directly to the culture medium or animal containing the host cell. Cell-membrane permeable, stable analogues of cAMP such as 8-Bromo-cAMP or dibutyryl cAMP may be used. Alternatively, the turpene compound forskolin can be used to stimulate the enzyme adenylate cyclase within the cell, thereby resulting in the cellular synthesis of cAMP.

In a preferred embodiment, 0.1–5 mM 8-Bromo-cAMP or dibutyryl cAMP is used in the method of the invention to stimulate transcription. Alternatively, any concentration of cAMP or an active derivative thereof may be used. The concentration which is required is limited only by the ability of that concentration to effectively induce the desired transcriptional response.

In addition to direct addition of cAMP or an active derivative thereof to the host cell or animal or medium containing the host cell, any hormone or other agent which is able to increase levels of cAMP in the host cell may be used, such as glucagon or β-adrenergic agents. The hormone or agent is limited only by the ability of the cell to respond to the hormone or agent in a cAMP dependent manner.

Although the exact mechanism of the regulatory steps are not known, it is believed that the presence of cAMP may influence the synthesis, activity, recognition ability and/or binding affinity of the CREB protein, which in turn, binds to the CRE palindrome, signalling the expression of the heterologous or recombinant gene.

The expressed heterologous protein or polypeptide may be isolated and purified in accordance with conventional conditions, such as extraction, precipitation, chromatography, affinity chromatography, electrophoresis, or the like.

Accordingly, it is within the scope of the methods of the present invention to stimulate the transcription of a heterologous translatable mRNA by cAMP where the increased levels of the heterologous, translatable mRNA results in an enhanced expression of a heterologous protein.

It is also within the methods of the invention to stimulate the synthesis of a heterologous but non-translatable RNA.

Accordingly, the recombinant gene may comprise any regulatory RNA sequence capable of being transcribed under direction of a CRE-regulatable promoter, but not able to be translated. By regulatory RNA is meant an RNA sequence capable of infuencing the transcription, processing or translation of another RNA sequence. In a preferred embodiment, the transcribed recombinant RNA sequence is an anti-sense RNA; that is, it is complementary to, and capable of hybridizing with, a known mRNA. According to the methods of the invention, upon the induction of the transcription of an anti-sense RNA under the direction of the cAMP-regulatable CREB-CRE recognition and binding, expression of the protein for which a mRNA codes would decrease or stop due to hybridization of the anti-sense strand of RNA with the sense strand. Accordingly, levels of the protein for which the mRNA codes fall. The mRNA Whose processing or translation is being inhibited by hybridization to the anti-sense RNA may be homologous to the host cell or heterologous to it. The method of the invention is especially applicable to the insertion of the minimal selectable region containing the CRE element operably-linked to a promoter directing the transcription of an anti-sense RNA sequence into the genome of the host cell, in a manner which allows it, in a cAMP dependent manner, to inhibit the over-expression of a protein detrimental to the viability of the cell. Such expression may utilize the CREB protein of the invention or the host's endogenous CREB protein.

The methods of the invention are also adaptable as methods of in vivo mutagenesis. For example, in yeast, by encoding a transposase in the cAMP- regulatable recombinant gene, transposition-dependent DNA mutational events may be placed under the control of cAMP. Cells exhibiting the desired mutant phenotype could then be isolated and characterized.

Alternatively the methods of the invention may be used as a method of mutagenesis which examines function of a protein by using the methods of the invention not to alter the genotype itself, but to effectively create cells deficient in a protein in response to a cAMP-directed transcription of an anti-sense RNA.

The advantage of the methods of the invention include their ability to provide reversible, acute methods of target-specific control of RNA expression or protein expression. The effect of the methods of the invention are reversible by decreasing, removing or metabolizing the levels of cAMP in the medium or cell. That is, by merely manipulating the levels of cAMP in the host cell for a desired period of time, expression of the gene operably-linked to the CRE element is controlled. In addition, the methods are acute because they are rapid and do not depend on the ability of the cell to replicate.

Having now generally described this invention, the same will be better understood by reference to specific examples, which are included herein for purposes of illustration only, and are not intended to be limiting unless otherwise specified.

EXAMPLES

A screening technique recently described by Singh and co-workers (Singh, H. et al., *Cell* 52:415 (1988)) was used to isolate a cDNA encoding an expressed protein that binds specifically to the CRE recognition site.

A primary screening of a human placental expression library with a radioactive synthetic CRE duplex probe yielded 23 positive recombinant phage plaques. After plaque purification through four successive screenings, only five positive clones remained. A recombinant phage that did not bind the radioactive probe was also plaque purified as a negative control. To establish the specificity of the binding of the radioactive probes, an array of synthetic oligonucleotide duplexes for which transcriptional activities and protein-binding characteristics have been elucidated in detail was utilized (Deutsch, P. J. et al., *Proc. Natl. Acad. Sci. USA* 85:7922 (1988); Deutsch, P. J. et al., *J. Bio. Chem.* (in press)). These duplex DNAs fall into three groups. The "active CRE's" consisted of the CRE octamer element flanked by several bases as they occur in the cAMP responsive chorionic gonadotropin α subunit and somatostatin genes and the collagenase gene in which the TRE heptamer was converted to a transcriptionally active CRE octamer (Deutsch, P. J. et al., *Proc. Natl. Acad. Sci. USA* 85:7922 (1988)). These sequences could impart transcriptional stimulation in response to 8-bromo-cAMP, when linked to a minimal promoter element, and could successfully compete for binding to a labeled "active CRE" in gel-shift assays. The corresponding TRE's produced band-shift patterns different from those of the CRE's and could not compete for binding to a labeled "active CRE." Finally, the "inactive CRE's" consisted of the CRE octamer in the contexts of the surrounding bases of the cAMP-unresponsive parathyroid hormone and glucagon genes and gave no transcriptional responses to 8-bromo-cAMP, nor could they produce specific gel-shift patterns or compete for binding to a labeled "active CRE." The first group consists of CRE sequences that contain the 8 bp palindrome 5'-TGACGTCA-3', flanked by several bases that are known to be permissive for both transcriptional activity and specific protein binding (Deutsch, P. J. et al., *Proc. Natl. Acad. Sci. USA* 85:7922 (1988); Deutsch, P. J. et al., *J. Bio. Chem.* (in press)). The second group consists of the identical oligonucleotide duplexes in which the core 8 bp element was mutated by the deletion of a single base to form the phorbol ester-responsive sequence 5'-TGAGTCA-3'. Although structurally very similar to CREs, these sequences exhibit functional and binding properties that allow exclusion of recombinant phage expressing TRE-binding proteins and other proteins that may recognize the CRE/TRE motifs non-specifically. The final group corresponds to "inactive CRE's." These oligonucleotide duplexes contain the CRE motif 5'-TGACGTCA-3', but are flanked by the sequences that are not permissive for either cAMP stimulated gene transcription or specific protein binding to the CRE.

Using this strategy only recombinant phage that bind the active CREs and not the mutant TREs or the inactive CREs were considered to be true positives. Only two of the five recombinant phages initially identified fulfilled all of the binding criteria specific to the native CREB protein from JEG-3 human choriocarcinoma cells (FIG. 1A). Analysis of the cDNA inserts from these two phages indicated that they contained identical 2.4 kb DNA inserts and probably represent duplicates of the same phage.

The specific procedure for detection of a positive recombinant fusion protein in a λ gt11 expression library containing human placental cDNAs was as follows:

IPTG-induced proteins from plates containing plaque-purified recombinant phages were bound to nitrocellulose filters and probed separately as described (Singh, H. et al., Cell 52:415 (1988)) with radioactive duplex oligonucleotides containing either an octomeric cAMP response element (CRE) or heptomeric TPA response element (TRE). The CRE-containing probe, but not the TRE-containing probe, was specifically bound by the protein encoded by the recombinant phage. The TRE-containing probe was designed according to the sequence outlined by Angel, P. et al., Cell 49:729 (1987). Previously the element has been shown to be incapable of competing for specific binding to labeled CRE-containing probes in gel-shift assays (Deutsch, P. J. et al., Proc. Natl. Acad. Sci. USA 85:7922 (1988)). The CRE probe differed from the TRE probe only by the additional C-G base-pair in parentheses, and was shown to impart a 15–30 fold stimulation of transcription in response to 8-bromo cAMP when placed upstream of a minimal promoter element.

5'-GATCCGGCTGAC(G)TCATCAAGCTA-3' CRE probe [SEQ ID NO:1]

3'-GCCGACTG(C)AGTAGTTCGATCTAG-5' TRE probe [SEQ ID NO:2]

The cDNA library was obtained from Clontech Laboratories, Inc., Palo Alto, Calif.

The radioactive CRE-containing probe used to select the recombinant phage will likewise bind to a protein present in a cell line of placental origin (JEG-3). Proteins in whole cell extracts of placental JEG-3 cells were separated by electrophoresis on a SDS-polyacrylamide gel and transferred to a nitrocellulose membrane. The membrane was incubated with the radioactive CRE probe, revealing two intensely radioactive bands corresponding to proteins of apparent molecular weights of 38 Kd and 36 Kd.

The Southwestern blot analysis of DNA binding activity in extracts of placental JEG-3 cells was as follows:

To demonstrate that the radioactive CRE-containing probe, used to select the recombinant phage, also binds to the 38 kd CREB protein from JEG-3 cells when immobilized on nitrocellulose membranes, a Southwestern analysis was performed. 50 ug of extract was separated on 10% denaturing SDS gels and then electrotransferred to nitrocellulose membranes. The membranes were then exposed as described (Singh, H. et al., Cell 52:415 (1988)) to radioactive binding site probes containing either a CRE probe or TRE probe. The labeled CRE probe bound strongly to proteins of 38 Kd and 36 Kd, and weakly to a 26 Kd protein in these extracts after 24 h of autoradiography. The specific binding of this protein(s) to the CRE element is a finding that is consistent with our earlier observations using UV-crosslinking (Deutsch, P J. et al., Proc. Natl. Acad. Sci. USA 85:7922 (1988)). However, the TRE probe gave only weak signals even after five days of autoradiography. These differences in signal strengths may be a consequence of the relative abundances of the proteins which bind these elements, or to differences in the degree of renaturation achieved after transfer to nitrocellulose. Molecular weights of marker proteins are shown on the left of the autoradiograms.

The protein encoded by the beta-galactosidase fusion gene was analyzed by UV-crosslinking in the presence or absence of unlabeled competitor DNAs followed by transfer to nitrocellulose.

Ultraviolet light cross-linking of lysogen extracts was used to demonstrate the galactosidase fusion protein responsible for specific binding to the labeled CRE probe. UV-crosslinking was performed as described earlier (Deutsch, P. J. et al., Proc. Natl. Acad. Sci. USA 85:7922 (1988)) using 50 ug of total protein from lysogen extracts from either the recombinant phage (center panel) or the negative control λ gt11 recombinant phage. The body-labeled, bromo-deoxyuridine incorporated probes were prepared by primed synthesis of the synthetic oligonucleotide 5'-AAAGCCAGAGGTGTCTGAC(G) TCATGCTTTATAACATCCTCTTGATTAG-CTA-3' [SEQ ID NO:3] using the 15 base primer 5'-TAGCTAATCAAGAGG-3'. The G in parentheses represents the single base insertion in the CRE relative to the TRE. After separating bound proteins on 10% SDS-gels, the proteins were transferred to nitrocellulose membranes and stained using anti-β-galactosidase antibodies. The major galactosidase species account for most of the specific binding. However, there were faint bands at lower molecular weights which presumably are due to binding to breakdown products of the apparent 137 Kd fusion protein, because negative control lysogens from the same Y1089 host cells showed no specific (or non-specific) binding to the CRE-containing probe. The specificity of binding to the CRE probe was confirmed by the lack of competition by the unlabeled TRE-containing probe.

Thus, the results confirmed that the B-galactosidase fusion protein was responsible for binding to the radioactive CRE-probe and that this binding is prevented in the presence of unlabeled CRE, but not unlabeled TRE, even at a 1000-fold molar excess.

Finally, to demonstrate that the fusion protein bound specifically to the CRE element in the context of a cellular promoter, a footprint analysis using the technique of digestion of DNA with exonuclease III was performed (Shalloway, D. et al., Cell 20:411 (1980)). The DNA construction comprised of the somatostatin CRE oligonucleotide duplex joined to the promoter sequence of the α-gonadotropin gene at position-100 (Deutsch, P. J. et al., Proc. Natl. Acad. Sci. USA 85:7922 (1988)). The bacterial lysogen extract and extracts of JEG-3 cells provide similar protection of the CRE.

The exonuclease III protection footprinting procedure of the CRE by DNA binding activity in lysogen extracts of phage G1 is described as follows:

The radioactive probe used consisted of a CRE flanked by the native sequences found surrounding this element in the somatostatin gene linked to a 144 bp fragment of the α-gonadotropin gene promoter extending from −100 to +44 (Deutsch, P. J. et al., Proc. Natl. Acad. Sci. USA 85:7922 (1988)). Both sense and antisense DNA strands were 5' end-labeled with $^{32}$P, cut with a restriction endonuclease and the single end labeled DNAs were isolated by electrophoresis on 4% polyacrylamide gels. Binding reactions with lysogen and JEG-3 whole cell extracts were performed as described previously for gel shift assays (Deutsch, P. J. et al., Proc. Natl. Acad. Sci. USA 85:7922 (1988); Deutsch, P. J. et al., *J. Bio. Chem.* (in press)). The radioactive probes in the presence of cell extracts were then exposed to 100 units of Exonuclease III for 10 minutes at 37° C. The final radioactive products were analyzed by electrophoresis on 8% sequencing gels.

The amino acid sequence of 326 residues (m.w. 35,024) deduced from the nucleotide sequence of the subcloned cDNA shows several interesting structural features characteristic of DNA-binding transcription factors belonging to a new class recognized as leucine zipper proteins (Landschultz, W. H. et al., *Science* 240:1760 (1988)) as shown in FIG. 1. This class of proteins includes myc, fos, C/EBP, GCN4 and c-jun. Comparisons of leucine zipper regions in the structure of CREB and then other DNA binding proteins are shown in FIG. 3. A hypothetical "leucine zipper sequence" in which four leucines are spaced seven residues apart is located near the carboxyl terminus of the protein. The sequence was recently proposed by Landschultz, Johnson, and McKnight (Landschultz, W. H. et al., *Science* 240:1760 (1988)) to be a region involved in the formation of protein homodimers or other protein-protein interactions.

A computer search for sequence similarities between CREB and c-jun revealed a single region of 61% identity of amino acids (19 of 31 residues) between positions 270 to 300 of CREB and 254 to 284 of c-jun as shown in FIG. 4. These regions of similarity are located adjacent to the leucine zipper regions of the two proteins and constitute basic domains in which over 50% of the residues are either arginine or lysine. There is also a similarity of sequence in this region with GCN4, a protein previously noted to have similarity to c-jun (Bohmann, D. et al., *Science* 238:1386 (1987); and Angel, P. et al. *Nature* 332:166 (1988)). Without being bound by the theory, the similarities of sequences limited to this basic domain suggests that all these proteins bind to similar palindromic sequences; either TGACGTCA (CREB) or TGAGTCA (c-jun and GCN4). The high positive charge densities of these regions of the DNA binding proteins would be compatible with close contact with the negatively charged phosphate backbone of the DNA.

Although no additional regions of similarity were discerned for the primary sequence of CREB and c-jun, comparison of the predicted secondary structures shows several notable features as shown in FIG. 5. As expected, the zipper regions at the carboxyl terminus of the two proteins consist entirely of alpha helix (Landschultz, W. H. et al., *Science* 240:1760 (1988)). However, the remainder of the sequences located amino terminal to the basic domains of both proteins are predominantly random coil and are highly acidic. The sequences of CREB (residues 1–268) and c-jun (residues 1–225) have ratios of acidic to basic residues of 2.5 and 2.0, respectively. The sequence of CREB between residues 1 to 268 contains 25 glutamic acids and aspartic acids and 11 lysines and arginines. The corresponding sequence of c-jun between residues 1 to 225 contains 22 glutamic acids and aspartic acids and 11 lysines and arginines. These acidic regions of transcriptional proteins may be important activator regions for interactions with the basic transcriptional machinery and have been referred to as "acid blobs" or "negative noodles" to describe the conformationally poorly-defined structure of a polypeptide that can function almost irrespective of sequence provided that there are a sufficient number of acidic residues clustered or scattered about (Sigler, P. S., *Nature* 333:210 (1988); Hope, I. A. et al., *Nature* 333:635 (1988); Ma, J. et al., *Cell* 48:847 (1987); and Gill, G. et al., *Cell* 51:121 (1987)).

What is claimed is:

1. A substantially purified DNA encoding cAMP-responsive transcription enhancer binding protein (CREB), said CREB having the amino acid sequence shown in FIG. 1.

2. Isolated DNA encoding CRE recognition or binding fragments of the protein encoding by the DNA of claim 1.

3. A construct comprising the DNA of claim 1 or the DNA of claim 2 encoding CRE recognition or binding fragments.

4. A construct comprising a promoter operably-linked to a heterologous gene coding for a protein or polypeptide and comprising the CRE palindrome with the nucleotide sequence TGACGTCA and the DNA of claim 1 wherein said CRE palindrome is operably-linked to said promoter.

5. A host cell transformed with the DNA of claim 1.

6. A method of increasing production of a heterologous protein or polypeptide, said method comprising:
   (a) transforming a eukaryotic host cell with a construct comprising
      (i) a minimum selectable region comprising a eukaryotic promoter operably-linked to a heterologous gene;
      (ii) a minimum selectable region comprising the CRE palindrome with the nucleotide sequence TGACGTCA operably linked to said promoter of said heterologous gene;
      (iii) a minimum selectable region comprising a eukaryotic promoter operably-linked to the DNA of claim 1;
   (b) culturing said transformed eukaryotic host cell under conditions selected for favorable growth of said host cell; and
   (c) adding cAMP to said host cell to stimulate said heterologous gene to express the encoded protein or polypeptide.

7. A method of increasing production of a heterologous protein or polypeptide, said method comprising:
   (a) transforming a eukaryotic host cell with a construct comprising
      (i) a minimum selectable region comprising a eukaryotic promoter operably-linked to a transcription unit;
      (ii) a minimum selectable region comprising the CRE palindrome with the nucleotide sequence TGACGTCA operably linked to said promoter of said transcription unit;
   (b) transforming said eukaryotic cell with a construct comprising
      (i) a minimum selectable region comprising a eukaryotic promoter operably-linked to the DNA of claim 1;
   (c) culturing said transformed eukaryotic host cell under conditions selected for favorable growth of said host cell; and
   (d) adding cAMP to said host cell to stimulate said heterologous gene to express the encoded protein or polypeptide.

8. A method for increasing transcription of DNA, said method comprising:
   (a) transforming a eukaryotic host cell with a construct comprising
      (i) a minimum selectable region comprising a eukaryotic promoter operably-linked to a heterologous gene;
      (ii) a minimum selectable region comprising the CRE palindrome with the nucleotide sequence TGACGTCA operably linked to said promoters of said heterologous gene;
      (iii) a minimum selectable region comprising a eukaryotic promoter operably-linked to the DNA of claim 1;
   (b) culturing said transformed eukaryotic host cell under conditions selected for favorable growth of said host cell; and
   (c) adding cAMP to said host cell to stimulate said heterologous gene to stimulate transcription of said heterologous gene.

9. A method for increasing transcription of DNA, said method comprising:
   transforming a eukaryotic host cell with a construct comprising
      (i) a minimum selectable region comprising a eukaryotic promoter operably-linked to a transcription unit;
      (ii) a minimum selectable region comprising the CRE palindrome with the nucleotide sequence TGACGTCA operably linked to said promoter of said transcription unit;
   (b) transforming said eukaryotic cell with a construct comprising
      (i) a minimum selectable region comprising a eukaryotic promoter operably-linked to the DNA of claim 1;
   (c) culturing said transformed eukaryotic host cell under conditions selected for favorable growth of said host cell; and
   (d) adding cAMP to said host cell to stimulate transcription of said transcription unit.

10. The method of claim 6, 7, 8 or 9 wherein the promoter operably-linked to the heterologous gene is the same sequence as the promoter operably-linked to said DNA of claim 1.

11. The method of claim 6, 7, 8 or 9 wherein the promoter operably-linked to the transcription unit uses RNA Polymerase II.

12. The method of claim 6, 7, 8 or 9 wherein the transcription unit codes for a transposase.

13. The method of claim 8 or 9 wherein the heterologous gene transcribes an anti-sense RNA.

14. A method for decreasing expression of a protein comprising:
    (a) transforming a eukaryotic host cell with the construct of claim 8 or 9 wherein said transcription unit transcribes the sequence of an anti-sense RNA;
    (b) culturing said transformed eukaryotic host cell under conditions selected for favorable growth of said host cell;
    (c) adding camp to said host cell to stimulate transcription of said anti-sense RNA; and
    (d) culturing said host cell under conditions favorable to hybridization of said anti-sense RNA to said mRNA whereby expression of said protein is decreased.

15. The method of claim 8 or 9, wherein said construct is integrated into the host's genome.

16. A construct comprising a promoter operably-linked to a heterologous gene coding for a protein or polypeptide and comprising the CRE palindrome with the nucleotide sequence TGACGTCA and nucleotides encoding a CRE recognition or binding fragment of the protein encoded by the DNA of claim 2 wherein said CRE palindrome is operably-linked to said promoter.

17. A host cell transformed with the DNA of claim 2.

18. The method of claim 14, wherein said mRNA is homologous to said host cell.

19. The method of claim 14, wherein said mRNA is heterologous to said host cell.

20. The method of claim 14 wherein said construct is integrated into the host's genome.

* * * * *

UNITED STATES PATENT AND TRADEMARK OFFICE
CERTIFICATE OF CORRECTION

PATENT NO. : 5,919,649

DATED : July 6, 1999

INVENTORS : Habener *et al.*

It is certified that an error appears in the above-identified patent and that said Letters Patent is hereby corrected as shown below.

On page 1, at line 1 of item [87] ("PCT Pub. No."), please delete "WO07/68496" and insert therein --WO 90/05745--;

On page 1, at line 2 of item [87] ("PCT Pub. Date"), please delete "May 22, 1991" and insert therein --May 31, 1990--;

Column 28, line 28, please delete "promoters" and insert therein --promoter--.

Signed and Sealed this

Seventeenth Day of April, 2001

Attest:

NICHOLAS P. GODICI

*Attesting Officer*   *Acting Director of the United States Patent and Trademark Office*

```
                              SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 24 base pairs
         (B) TYPE: nucleic acid
         (C) STRANDEDNESS: both
         (D) TOPOLOGY: linear (ii) MOLECULE TYPE: DNA (xi) SEQUENCE DESCRIPTION: SEQ ID NO:1:

GATCCGGCTG ACGTCATCAA GCTA                                              24

(2) INFORMATION FOR SEQ ID NO:2:

(i) SEQUENCE CHARACTERISTICS:
         (A) LENGTH: 24 base pairs
         (B) TYPE: nucleic acid
         (C) STRANDEDNESS: both
         (D) TOPOLOGY: linear (ii) MOLECULE TYPE: DNA (xi) SEQUENCE DESCRIPTION: SEQ ID NO:2:

GATCTAGCTT GATGACGTCA GCCG                                              24
```

(2) INFORMATION FOR SEQ ID NO:3:

(i) SEQUENCE CHARACTERISTICS:
        (A) LENGTH: 51 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:3:

```
AAAGCCAGAG GTGTCTGACG TCATGCTTTA TAACATCCTC TTGATTAGCT A          51
```

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:4:

```
TAGCTAATCA AGAGG                                                  15
```

(2) INFORMATION FOR SEQ ID NO:5:

(i) SEQUENCE CHARACTERISTICS:
        (A) LENGTH: 2475 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: CDS
        (B) LOCATION: 126..1106

(xi) SEQUENCE DESCRIPTION: SEQ ID NO:5:

```
GAATTCGGGC GCGCCGGAGG TGTAGTTTGA CGCGGTGTGT TACGTGGGGG AGAGAATAAA       60

ACTCCAGCGA GATCCGCGCC GTGAACGAAA GCAGTGACGG AGGAGCTTGT ACCACCGGTA      120

ACTAA ATG ACC ATG GAA TCT GGA GCC GAG AAC CAG CAG AGT GGA CAT         167
      Met Thr Met Glu Ser Gly Ala Glu Asn Gln Gln Ser Gly His
        1               5                  10

GCA GCT GTA ACA GAA GCT GAA AAC CAA CAA ATG ACA GTT CAA GCC CAG       215
Ala Ala Val Thr Glu Ala Glu Asn Gln Gln Met Thr Val Gln Ala Gln
 15              20                  25                  30

CCA CAG ATT GCC ACA TTA GCC CAG GTA TCT ATG CCA GCA GCT CAT GCA       263
Pro Gln Ile Ala Thr Leu Ala Gln Val Ser Met Pro Ala Ala His Ala
             35                  40                  45

ACA TCA TCT GCT CCC ACC GTA ACT CTA GTA CAG CTG CCC AAT GGG CAG       311
Thr Ser Ser Ala Pro Thr Val Thr Leu Val Gln Leu Pro Asn Gly Gln
         50                  55                  60

ACA GTT CAA GTC CAT GGA GTC ATT CAG GCG GCC CAG CCA TCA GTT ATT       359
Thr Val Gln Val His Gly Val Ile Gln Ala Ala Gln Pro Ser Val Ile
             65                  70                  75

CAG TCT CCA CAA GTC CAA ACA GTT CAG ATT TCA ACT ATT GCA GAA AGT       407
Gln Ser Pro Gln Val Gln Thr Val Gln Ile Ser Thr Ile Ala Glu Ser
 80                  85                  90

GAA CAT TCA CAG GAG TCA GTG GAT AGT GTA ACT GAT TCC CAA AAC CGA       455
Glu His Ser Gln Glu Ser Val Asp Ser Val Thr Asp Ser Gln Asn Arg
 95                 100                 105                 110
```

| | | |
|---|---|---|
| AGG GAA ATT CTT TCA AGG AGG CCT TCC TAC AGG AAA ATT TTG AAT GAC<br>Arg Glu Ile Leu Ser Arg Arg Pro Ser Tyr Arg Lys Ile Leu Asn Asp<br>115 120 125 | | 503 |
| TTA TCT TCT GAT GCA CCA GGA GTG CCA AGG ATT GAA GAA GAG AAG TCT<br>Leu Ser Ser Asp Ala Pro Gly Val Pro Arg Ile Glu Glu Glu Lys Ser<br>130 135 140 | | 551 |
| GAA GAG GAG ACT TCA GCA CCT GCC ATC ACC ACT GTA ACG GTG CCA ACT<br>Glu Glu Glu Thr Ser Ala Pro Ala Ile Thr Thr Val Thr Val Pro Thr<br>145 150 155 | | 599 |
| CCA ATT TAC CAA ACT AGC AGT GGA CAG TAT ATT GCC ATT ACC CAG GGA<br>Pro Ile Tyr Gln Thr Ser Ser Gly Gln Tyr Ile Ala Ile Thr Gln Gly<br>160 165 170 | | 647 |
| GGA GCA ATA CAG CTG GCT AAC AAT GGT ACC GAT GGG GTA CAG GGC CTG<br>Gly Ala Ile Gln Leu Ala Asn Asn Gly Thr Asp Gly Val Gln Gly Leu<br>175 180 185 190 | | 695 |
| CAA ACA TTA ACC ATG ACC AAT GCA GCA GCC ACT CAG CCG GGT ACT ACC<br>Gln Thr Leu Thr Met Thr Asn Ala Ala Ala Thr Gln Pro Gly Thr Thr<br>195 200 205 | | 743 |
| ATT CTA CAG TAT GCA CAG ACC ACT GAT GGA CAG CAG ATC TTA GTG CCC<br>Ile Leu Gln Tyr Ala Gln Thr Thr Asp Gly Gln Gln Ile Leu Val Pro<br>210 215 220 | | 791 |
| ACC AAC CAA GTT GTT GTT CAA GCT GCC TCT GGA GAC GTA CAA ACA TAC<br>Thr Asn Gln Val Val Val Gln Ala Ala Ser Gly Asp Val Gln Thr Tyr<br>225 230 235 | | 839 |
| CAG ATT CGC ACA GCA CCC ACT AGC ACT ATT GCC CCT GGA GTT GTT ATG<br>Gln Ile Arg Thr Ala Pro Thr Ser Thr Ile Ala Pro Gly Val Val Met<br>240 245 250 | | 887 |
| GCA TCC TCC CCA GCA CTT CCT ACA CAG CCT GCT GAA GAA GCA CCA CGA<br>Ala Ser Ser Pro Ala Leu Pro Thr Gln Pro Ala Glu Glu Ala Pro Arg<br>255 260 265 270 | | 935 |
| AAG AGA GAG GTC CGT CTA ATG AAG AAC AGG GAA GCA GCT CGA GAG TGT<br>Lys Arg Glu Val Arg Leu Met Lys Asn Arg Glu Ala Ala Arg Glu Cys<br>275 280 285 | | 983 |
| CGT AGA AAG AAG AAA GAA TAT GTG AAA TGT TTA GAA AAC AGA GTG GCA<br>Arg Arg Lys Lys Lys Glu Tyr Val Lys Cys Leu Glu Asn Arg Val Ala<br>290 295 300 | | 1031 |
| GTG CTT GAA AAT CAA AAC AAG ACA TTG ATT GAG GAG CTA AAA GCA CTT<br>Val Leu Glu Asn Gln Asn Lys Thr Leu Ile Glu Glu Leu Lys Ala Leu<br>305 310 315 | | 1079 |
| AAG GAC CTT TAC TGC CAC AAA TCA GAT TAATTTGGGA TTTAAATTTT<br>Lys Asp Leu Tyr Cys His Lys Ser Asp<br>320 325 | | 1126 |
| CACCTGTTAA CGTGGAAAAT GGACTGGCTT GGCCACAACC TGAAAGACAA AATAAACATT | | 1186 |
| TTATTTTCTA ACATTTCTT TTTTTCTATG CGCAAAACTG CCTGAAAGCA ACTACAGAAT | | 1246 |
| TTCATTCATT TGTGCTTTTG CATTAAACTG TGAATGTTCC AACACCTGCC TCCACTTCTC | | 1306 |
| CCCTCAAGAA ATTTTCAACG CCAGGAATCA TGAAGAGACT TCTGCTTTTC AACCCCCACC | | 1366 |
| CTCCTCAAGA AGTAATAATT TGTTTACTTG TAAATTGATG GGAGAAATGA GGAAAAGAAA | | 1426 |
| ATCTTTTTAA AAATGATTTC AAGGTTTGTG CTGAGCTCCT TGATTGCCTT AGGGACAGAA | | 1486 |
| TTACCCCAGC CTCTTGAGCT GAAGTAATGT GTGGGCCGCA TGCATAAAGT AAGTAAGGTG | | 1546 |
| CAATGAAGAA GTGTTGATTG CCAAATTGAC ATGTTGTCAC ATTCTCATTG TGAATTATGT | | 1606 |
| AAAGTTGTTA AGAGACATAC CCTCTAAAAA AGAACTTTAG CATGGTATTG AAGGAATTAG | | 1666 |
| AAATGAATTT GCAGTGCTTT TTATGTATGT TGTCTTCTTC AATACTGAAA ATTTGTCCTT | | 1726 |
| GGTTCTTAAA AGCATTCTGT ACTAATACAG CTCTTCCATA GGGCAGTTGT TGCTTCTTAA | | 1786 |
| TTCAGTTCTG TATGTGTTCA ACATTTTTGA ATACATTAAA AGAAGTAACC AACTGAACGA | | 1846 |

```
CAAAGCATGG TATTTGAATT TTAAATTAAA GCAAAGTAAA TAAAAGTACA AAGCATATTT    1906

TAGTTAGTAC TAAATTCTTA GTAAAATGCT GATCAGTAAA CCAATCCCTT GAGTTATATA    1966

ACAAGATTTT TAAATAAATG TTATTGTCCT CACCTTCAAA AATATTTATA TTGTCACTCA    2026

TTTACGTAAA AAGATATTTC TAATTTACTG TTGCCCATTG CACTTACATA CCACCACCAA    2086

GAAAGCCTTC AAGATGTCAA ATAAAGCAAA GTGATATATA TTTGTTTATG AAATGTTACA    2146

TGTAGAAAAA TACTGATTTT AAATATTTTC CATATTAACA ATTTAACAGA GAATCTCTAG    2206

TGAATTTTTT AAATGAAAGA AGTTGTAAGG ATATAAAAAG TACAGTGTTA GATGTGCACA    2266

AGGAAAGTTA TTTTCAGACA TATTTGAATG ACTGCTGTAC TGCAATATTT GGATTGTCAT    2326

TCTTACAAAA CATTTTTTTG TTCTCTTCTA AAAACACTAG TTATTAGTTC TGCTTTAGCT    2386

TTCCAATATG CTGTATAGCC TTTGTCATTT TATAATTTTA ATTCCTGATT AAAACAGTCT    2446

GTATTTGTGT ATATCATCCC CCCGAATTC                                     2475
```

(2) INFORMATION FOR SEQ ID NO:6:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO:6:

```
Met Thr Met Glu Ser Gly Ala Glu Asn Gln Gln Ser Gly His Ala Ala
 1               5                  10                  15

Val Thr Glu Ala Glu Asn Gln Gln Met Thr Val Gln Ala Gln Pro Gln
                20                  25                  30

Ile Ala Thr Leu Ala Gln Val Ser Met Pro Ala Ala His Ala Thr Ser
            35                  40                  45

Ser Ala Pro Thr Val Thr Leu Val Gln Leu Pro Asn Gly Gln Thr Val
        50                  55                  60

Gln Val His Gly Val Ile Gln Ala Ala Gln Pro Ser Val Ile Gln Ser
 65                  70                  75                  80

Pro Gln Val Gln Thr Val Gln Ile Ser Thr Ile Ala Glu Ser Glu His
                85                  90                  95

Ser Gln Glu Ser Val Asp Ser Val Thr Asp Ser Gln Asn Arg Arg Glu
               100                 105                 110

Ile Leu Ser Arg Arg Pro Ser Tyr Arg Lys Ile Leu Asn Asp Leu Ser
           115                 120                 125

Ser Asp Ala Pro Gly Val Pro Arg Ile Glu Glu Lys Ser Glu Glu
       130                 135                 140

Glu Thr Ser Ala Pro Ala Ile Thr Thr Val Thr Val Pro Thr Pro Ile
145                 150                 155                 160

Tyr Gln Thr Ser Ser Gly Gln Tyr Ile Ala Ile Thr Gln Gly Gly Ala
               165                 170                 175

Ile Gln Leu Ala Asn Asn Gly Thr Asp Gly Val Gln Gly Leu Gln Thr
           180                 185                 190

Leu Thr Met Thr Asn Ala Ala Ala Thr Gln Pro Gly Thr Thr Ile Leu
       195                 200                 205

Gln Tyr Ala Gln Thr Thr Asp Gly Gln Gln Ile Leu Val Pro Thr Asn
   210                 215                 220

Gln Val Val Val Gln Ala Ala Ser Gly Asp Val Gln Thr Tyr Gln Ile
225                 230                 235                 240

Arg Thr Ala Pro Thr Ser Thr Ile Ala Pro Gly Val Val Met Ala Ser
```

```
                        245                 250                 255
Ser Pro Ala Leu Pro Thr Gln Pro Ala Glu Glu Ala Pro Arg Lys Arg
                260                 265                 270
Glu Val Arg Leu Met Lys Asn Arg Glu Ala Ala Arg Glu Cys Arg Arg
            275                 280                 285
Lys Lys Lys Glu Tyr Val Lys Cys Leu Glu Asn Arg Val Ala Val Leu
        290                 295                 300
Glu Asn Gln Asn Lys Thr Leu Ile Glu Glu Leu Lys Ala Leu Lys Asp
305                 310                 315                 320
Leu Tyr Cys His Lys Ser Asp
                325
```

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:7:

```
Leu Thr Ser Asp Asn Asp Arg Leu Arg Lys Arg Val Glu Gln Leu Ser
1               5                   10                  15
Arg Glu Leu Asp Thr Leu Arg Gly Ile Phe Arg
            20                  25
```

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:8:

```
Leu Glu Glu Lys Val Lys Thr Leu Lys Ala Gln Asn Ser Glu Leu Ala
1               5                   10                  15
Ser Thr Ala Asn Met Leu Arg Glu Gln Val Ala
            20                  25
```

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:9:

```
Leu Glu Asp Lys Val Glu Glu Leu Leu Ser Lys Asn Tyr His Leu Glu
1               5                   10                  15
Asn Glu Val Ala Arg Leu Lys Lys Leu Val Gly
            20                  25
```

(2) INFORMATION FOR SEQ ID NO:10:

(i) SEQUENCE CHARACTERISTICS:
        (A) LENGTH: 27 amino acids
        (B) TYPE: amino acid (C) STRANDEDNESS: both
        (D) TOPOLOGY: linear (ii) MOLECULE TYPE: peptide (xi) SEQUENCE DESCRIPTION: SEQ ID NO:10:

Leu Gln Ala Glu Thr Asp Gln Leu Glu Asp Lys Lys Ser Ala Leu Gln
1               5                   10                  15

Thr Glu Ile Ala Asn Leu Leu Lys Glu Lys Glu
            20                  25

(2) INFORMATION FOR SEQ ID NO:11:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:11:

Leu Gln Ala Glu Glu His Gln Leu Leu Leu Glu Lys Glu Lys Leu Gln
1               5                   10                  15

Ala Arg Gln Gln Gln Leu Leu Lys Lys Ile Glu
            20                  25

(2) INFORMATION FOR SEQ ID NO:12:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:12:

Leu Val Gly Ala Glu Lys Arg Met Ala Thr Glu Lys Arg Gln Leu Arg
1               5                   10                  15

Cys Arg Gln Gln Gln Leu Gln Lys Arg Ile Ala
            20                  25

(2) INFORMATION FOR SEQ ID NO:13:

(i) SEQUENCE CHARACTERISTICS:
        (A) LENGTH: 27 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:13:

Leu Thr Ser Glu Lys Asp Leu Leu Arg Lys Arg Arg Glu Gln Leu Lys
1               5                   10                  15

His Lys Leu Glu Gln Leu Arg Asn Ser Gly Ala
            20                  25

(2) INFORMATION FOR SEQ ID NO:14:

(i) SEQUENCE CHARACTERISTICS:
        (A) LENGTH: 60 amino acids
        (B) TYPE: amino acid
        (C) STRANDEDNESS: both
        (D) TOPOLOGY: linear (ii) MOLECULE TYPE: peptide (xi) SEQUENCE DESCRIPTION: SEQ ID NO:14:

```
Ile Asp Met Glu Ser Gln Glu Arg Ile Lys Ala Glu Arg Lys Arg Met
1               5                   10                  15

Arg Asn Arg Ile Ala Ala Ser Lys Cys Arg Lys Arg Lys Leu Glu Arg
            20                  25                  30

Ile Ala Arg Leu Glu Glu Lys Val Lys Thr Leu Lys Ala Gln Asn Ser
            35              40                  45

Glu Leu Ala Ser Thr Ala Asn Met Leu Arg Glu Gln
    50              55                  60
```